United States Patent
Gerlach

(10) Patent No.: US 12,357,780 B2
(45) Date of Patent: Jul. 15, 2025

(54) FAN UNIT FOR A VENTILATOR

(71) Applicant: Loewenstein Medical Technology S.A., Luxembourg (LU)

(72) Inventor: Angela Gerlach, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 643 days.

(21) Appl. No.: 17/596,666

(22) PCT Filed: May 18, 2020

(86) PCT No.: PCT/EP2020/025230
§ 371 (c)(1),
(2) Date: Dec. 16, 2021

(87) PCT Pub. No.: WO2020/253983
PCT Pub. Date: Dec. 24, 2020

(65) Prior Publication Data
US 2022/0305224 A1    Sep. 29, 2022

(30) Foreign Application Priority Data

Jun. 20, 2019 (DE) .......................... 102019116718.3

(51) Int. Cl.
F04D 29/42    (2006.01)
A61M 16/00    (2006.01)
(Continued)

(52) U.S. Cl.
CPC .... A61M 16/0066 (2013.01); A61M 16/0054 (2013.01); F04D 29/30 (2013.01);
(Continued)

(58) Field of Classification Search
CPC .......... A61M 16/0057; A61M 16/0066; A61M 16/0054; F04D 29/30; F04D 29/4213; F04D 29/4226; F04D 29/441; F04D 29/281
See application file for complete search history.

(56) References Cited

U.S. PATENT DOCUMENTS 8,973,576 B2    3/2015    Kenyon et al.
10,323,650 B2    6/2019    Kosaka et al.
(Continued)

FOREIGN PATENT DOCUMENTS

CN    205536443 U    8/2016
CN    106989062 A    7/2017
(Continued)

Primary Examiner — Sabbir Hasan
(74) Attorney, Agent, or Firm — Abel Schillinger, LLP

(57) ABSTRACT

Fan unit for a ventilator, comprising a housing with a suction connector which forms an inlet duct for the suction-side inflow of a fluid into the housing, a pressure connector which forms an outlet duct for the pressure-side outflow of the fluid from the housing, and a fan impeller mounted rotatably in the housing and being configured, by rotation, to suck in the fluid via the suction connector and to convey it through the inlet duct into the housing, and to eject the fluid again via the pressure connector and to convey it through the outlet duct out of the housing. The suction connector has at least one flow guiding element on its inner face which faces the inlet duct and defines an inlet duct nominal diameter, by which element an inlet duct internal diameter differing at least in sections from the inlet duct nominal diameter is set.

20 Claims, 7 Drawing Sheets

(51) Int. Cl.
*F04D 29/30* (2006.01)
*F04D 29/44* (2006.01)

(52) U.S. Cl.
CPC ..... *F04D 29/4213* (2013.01); *F04D 29/4226* (2013.01); *F04D 29/441* (2013.01)

(56) References Cited

U.S. PATENT DOCUMENTS

| | | |
|---|---|---|
| 2011/0236190 A1 | 9/2011 | Chen et al. |
| 2012/0199129 A1 | 8/2012 | Kenyon et al. |
| 2012/0285454 A1 | 11/2012 | Nibu et al. |
| 2016/0201693 A1 | 7/2016 | An et al. |
| 2017/0130723 A1 | 5/2017 | Kosaka et al. |
| 2018/0064894 A1* | 3/2018 | Fu ................... F04D 29/4253 |
| 2020/0009337 A1 | 1/2020 | Higashiyama |
| 2020/0191163 A1 | 6/2020 | Rathgeb et al. |

FOREIGN PATENT DOCUMENTS

| | | | |
|---|---|---|---|
| EP | 2947328 A1 | 11/2015 | |
| EP | 3048430 A1 | 7/2016 | |
| EP | 2947328 B1 * | 12/2018 | ........ A61M 16/0066 |
| JP | S54105903 U | 7/1979 | |
| JP | S57066297 U | 1/1982 | |
| JP | S59029799 A | 2/1984 | |
| JP | S59163197 U | 11/1984 | |
| JP | H08247090 A | 9/1996 | |
| JP | 2002122097 A | 4/2002 | |
| JP | 2006002650 A | 1/2006 | |
| JP | 2009024595 A | 2/2009 | |
| JP | 2010190151 A | 9/2010 | |
| JP | 2018062894 A | 4/2018 | |
| WO | 2014178475 A1 | 11/2014 | |
| WO | 2019014173 A1 | 1/2019 | |

* cited by examiner

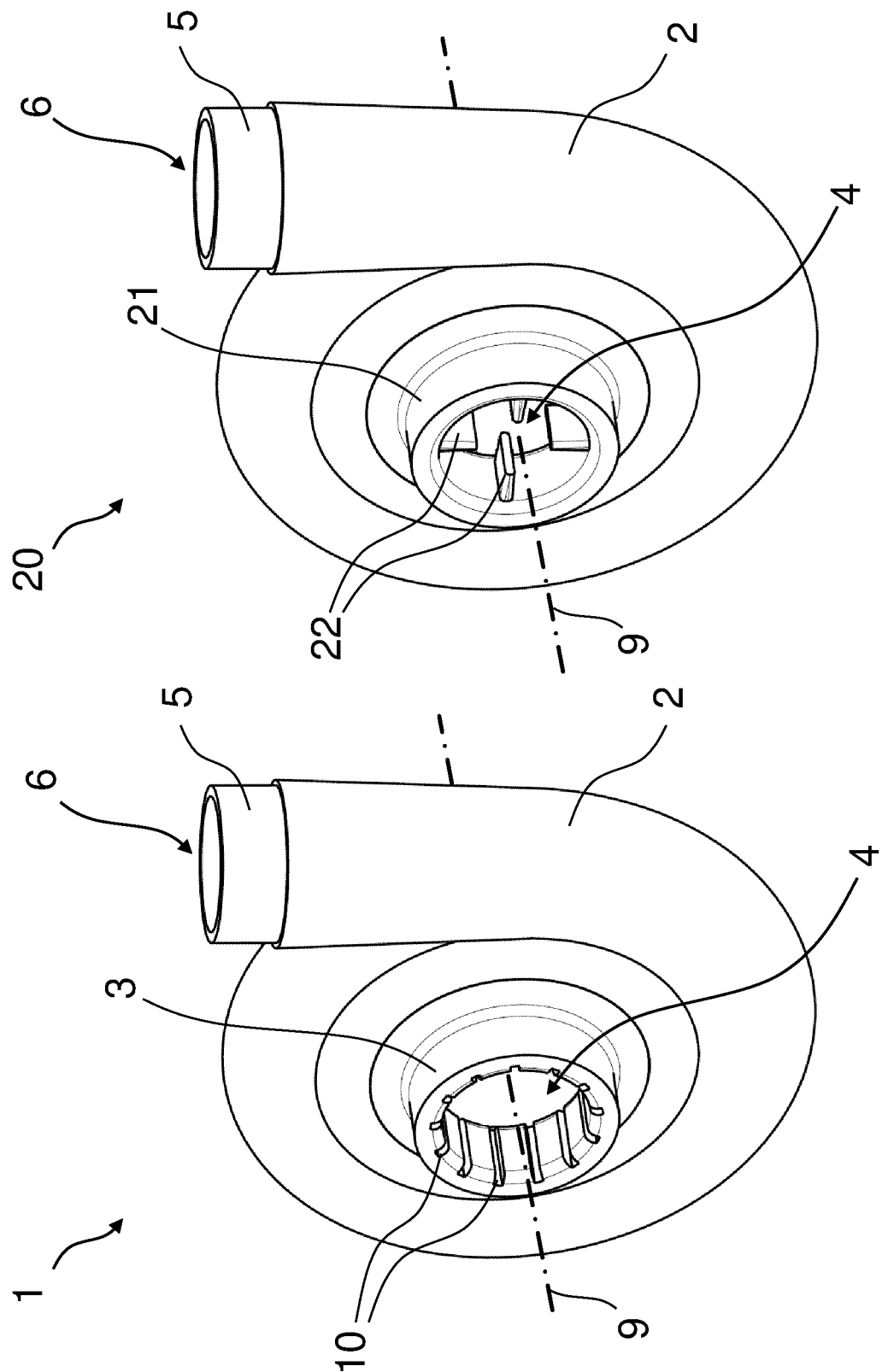

FAN UNIT FOR A VENTILATOR

BACKGROUND OF THE INVENTION

1. Field of the Invention

The present invention relates to a fan unit for a ventilator, in particular a fan unit with a housing and a fan impeller which is mounted rotatably in the housing and by means of which, by way of rotation, a fluid can be sucked in through an inlet duct of the housing and can subsequently be ejected again through an outlet duct of the housing.

2. Discussion of Background Information

Different embodiments of fan units of this type for ventilators for the ventilation, in particular, of persons with insufficient or suspended spontaneous respiration are known. For example, EP 2 947 328 A1 describes a fan unit with an electric motor, an impeller wheel which is driven by the latter, and a housing which receives the impeller wheel and the electric motor. The previously known fan unit is a free intake fan unit, that is to say it does not have a suction connector on the suction side, with the result that the breathing gas is not sucked in via a hose which is connected on the suction side to the fan unit. Said free intake fan unit can be received, for example, in a blower box of the ventilator.

Against this background, the present invention is based on the object of providing a fan unit for a ventilator, which fan unit has improved operating performance and relates both to a free intake fan unit and to a non-free intake fan unit. Thus, in particular, a fluid which is sucked into the housing on the suction side by means of the fan impeller, for example a breathing gas, is to be capable of flowing out of the housing again on the pressure side at a predefined pressure; the outflow pressure of the fan unit is to achieve higher values in comparison with the outflow pressure of conventional fan units for ventilators at the same rotational speed of the fan impeller, and/or the rotational speed of the fan unit is to be capable of being reduced at an identical outflow pressure of the fan unit in comparison with conventional fan units.

Said object is achieved by way of a fan unit with the features set forth in the independent claim. Further, particularly advantageous refinements of the invention are disclosed by the dependent claims.

It is to be noted that the features which are specified individually in the claims can also be combined with one another in any desired, technically appropriate way, and can specify further refinements of the invention. The description additionally characterizes and specifies the invention, in particular, in conjunction with the figures.

SUMMARY OF THE INVENTION

According to the invention, a fan unit for ventilators for the ventilation, in particular, of persons with insufficient or suspended spontaneous respiration comprises a housing with a suction connector, the suction connector forming an inlet duct for the suction-side inflow of a fluid, for example a breathing gas, into the housing. Furthermore, the housing comprises a pressure connector which forms an outlet duct for the pressure-side outflow of the fluid from the housing. Furthermore, the fan unit according to the invention comprises a fan impeller which is mounted rotatably in the housing. Said fan impeller is configured and arranged, by way of rotation, to suck in the fluid via the suction connector and to convey it through the inlet duct into the housing, and to eject the fluid again via the pressure connector and to convey it through the outlet duct out of the housing. It is to be understood that the rotation of the fan impeller can be brought about, for example, in a motorized manner, preferably by means of an electric motor, without being restricted thereto, however. A manually driven rotation of the fan impeller is likewise conceivable.

The suction connector has an inner face which faces the inlet duct. In other words, the inner face of the suction connector delimits the inlet duct in the radial direction to the outside. Therefore, an inlet duct nominal diameter is defined by way of the inner face of the suction connector. According to the invention, the suction connector has at least one flow guiding element on its inner face, which flow guiding element sets an inlet duct internal diameter which differs from the inlet duct nominal diameter. Here, "deviating" in the sense of the present invention is to be understood to mean a size difference between the two duct diameters which is such that it certainly does not fall within the production-induced tolerance range of a suction connector, but rather is the result of targeted action. Production-induced size differences of the two abovementioned duct diameters which lie within the conventional manufacturing tolerances which are specified for the manufacturing of the suction connector are not suitable as a consequence for substantiating a size difference between the inlet duct nominal diameter and the inlet duct internal diameter in the sense of the invention.

In contrast to a smooth, planar inner face of a conventional suction connector, the suction connector of the fan unit according to the invention as a consequence does not have a planar inner face. Rather, the inner face of the suction connector according to the invention is structured by way of the at least one flow guiding element, as a result of which the flow of the fluid which is sucked in, for example a gas or breathing gas, can be influenced, that is to say can be controlled, in a way which corresponds to the contour of the flow guiding element. Those regions of the inner face of the suction connector which are not provided with the flow guiding element and define the inlet duct internal diameter can still be of smooth and planar configuration, without being necessarily restricted thereto, however.

In particular, a pressure increase of the fluid which is sucked in by way of the fan impeller can be achieved solely by way of the provision of the at least one flow guiding element for locally changing the inlet duct internal diameter. At an identical rotational speed of the fan impeller of the fan unit according to the invention in comparison with conventional fan units, this in turn makes an increase of the pressure of the fluid which flows out on the pressure side possible. As an alternative, in the case of an identical fluid pressure in the outlet duct of the pressure connector in comparison with conventional fan units, the rotational speed of the fan impeller in the case of the fan unit according to the invention can also be decreased. As a result, the operational efficiency of the fan unit according to the invention can be improved, and the smooth running of the fan impeller can be increased, vibrations, mechanical wear, for example on fan impeller bearings, and noise development of the fan unit can be decreased by way of a reduction of the rotational speed.

The fan unit according to the invention is not a free intake fan unit as a result of the suction connector which is provided on the suction side, is differentiated from the housing per se by way of an elongate extent which forms the inlet duct, and can project or protrudes, for example, from the actual outer contour of the housing. Rather, the suction connector can be connected to a hose, via which the fluid is sucked into the inlet duct.

The housing of the fan unit disclosed in the present case can be a substantially closed housing unit which surrounds the fan impeller in such a way that the fluid flow as described herein, namely intake of the fluid on the suction side of the fan unit and ejecting of the fluid on the pressure side of the fan unit, in particular with an increased fluid pressure in comparison with the suction side, can be generated by way of the rotation of the fan impeller. In addition, a motor which drives the fan impeller, if provided, for example a drive motor which is operated by electric motor, can also be received in the housing. This is not absolutely necessary, however.

The cross-sectional area of the inlet duct can have a round shape, for example circular, elliptical and the like. It can also have an angular shape, for example rectangular, square, trapezoidal, generally polygonal and the like.

In accordance with one advantageous refinement of the invention, the flow guiding element is a rib (also called a fin, web, lamella and the like herein) which projects from the inner face of the suction connector. In other words, the rib protrudes from the inner face in the radial direction inward into the inlet duct. Accordingly, the rib decreases the inlet duct internal diameter which is set by it locally with respect to the inlet duct nominal diameter which is set by the regions of the inner face which are not provided with the rib. Here, the inlet duct internal diameter is set by way of the spacing between an end side of the rib, which end side protrudes furthest to the inside in the radial direction into the inlet duct, and the bounding face which delimits the inlet duct in a manner which lies diametrically opposite. Said bounding face can be that inner face of the suction connector which defines the inlet duct nominal diameter, but it can likewise be a face of a further flow guiding element which lies diametrically opposite the first-mentioned rib.

In accordance with a further advantageous refinement of the invention, the flow guiding element is a groove which is made in the inner face of the suction connector. The groove which is a depression which is made in the inner face in the radial direction toward the outside accordingly increases the inlet duct internal diameter locally in comparison with the inlet duct nominal diameter which is set by the regions of the inner face which are not provided with a groove. Here, the inlet duct internal diameter is set by way of the spacing in the radial direction between a groove bottom which lies further to the outside in the radial direction and a bounding face which delimits the inlet duct in a manner which lies diametrically opposite. Said bounding face can be that inner face of the suction connector which defines the inlet duct nominal diameter, but it can likewise be a face of a further flow guiding element which lies diametrically opposite the first-mentioned groove.

On account of the local decrease or increase of the duct internal diameter with respect to the inlet duct nominal diameter, the flow guiding element which is configured as a groove or rib makes different, targeted influencing of the fluid flow, in particular a pressure increase, in the inlet duct possible. It has been shown that a flow guiding element which is configured as a groove influences the pressure characteristic curve of the fluid flow to a greater extent than a flow guiding element which is configured as a rib.

In accordance with a further advantageous refinement, a plurality of flow guiding elements are arranged distributed equidistantly, that is to say at identical spacings from one another, over the circumference of the inner face of the suction connector. The fluid flow and therefore the fluid pressure, in particular a pressure increase, in the inlet duct can be influenced in a further targeted manner by way of the number of flow guiding elements which are arranged overall distributed circumferentially on the inner face.

A further advantageous refinement of the invention provides that, in the case of the provision of a plurality of ribs arranged distributed circumferentially on the inner face of the suction connector as flow guiding elements, said ribs extend in the radial direction as far as the center axis (also called an axis of symmetry herein) of the suction connector and are in contact with one another there. They can be connected integrally to one another at their contact point in the inlet duct, which is not absolutely necessary, however. In other words, as viewed in the cross section of the suction connector, the ribs form at least one web which crosses the inlet duct completely in the radial direction (in the case of two ribs which are arranged diametrically and make contact with one another) or a star-shaped arrangement (in the case of three, four, five or more ribs which are arranged in a distributed manner). It is to be noted that, in the case of the present refinement with ribs which make contact on the center axis, the inlet duct internal diameter which is defined by way of them and is decreased in comparison with the inlet duct nominal diameter assumes its absolute minimum value, namely the value zero.

In accordance with a further advantageous refinement of the invention, the flow guiding element extends in its longitudinal extent direction parallel to the center axis of the suction connector. In other words, the flow guiding element is oriented in its longitudinal extent direction in an axially parallel manner with respect to the center axis of the suction connector. As a result, the pressure change brought about by way of the flow guiding element, in particular the pressure increase, of the fluid which flows through the suction connector can be achieved particularly effectively.

In accordance with another advantageous refinement of the invention, the flow guiding element extends in its longitudinal extent direction at an angle in an inclined manner with respect to the center axis of the suction connector, and therefore accordingly not in an axially parallel manner with respect to the center axis. Depending on the angle of inclination of the longitudinal extent of the flow guiding element, the pressure increase which is brought about by way of this in the inlet duct can be controlled in a highly precise manner, in particular can be attenuated in a targeted manner in a desired way in comparison with the axially parallel arrangement.

In accordance with a further preferred refinement of the invention, the abovementioned angle or angle of inclination of the longitudinal extent of the flow guiding element with respect to the center axis of the suction connector or inlet duct is greater than 0° and less than or equal to 45°. It is to be understood that, in the sense of the invention, the longitudinal extent direction of the flow guiding element still extends mainly in the direction of the center axis of the suction connector in this refinement. Furthermore, it is to be understood that, depending on the definition of the angle of inclination with respect to the center axis of the suction connector, the angular range of less than 0° to greater than or equal to −45° is to be considered equivalent to the above-specified angular range of greater than 0° and less than or equal to 45°.

In accordance with a further preferred refinement of the invention, the ratio of the inlet duct internal diameter to the inlet duct nominal diameter lies between 0.6 and 1.4, preferably between 0.7 and 1.3, more preferably between 0.75 and 1.25. It has been shown that the desired pressure changes in the inlet duct of the suction connector can be achieved most effectively by way of said ratios. It is to be understood that a ratio of the inlet duct internal diameter to the inlet duct nominal diameter of less than one can be achieved by way of the provision of at least one rib-shaped/web-shaped flow guiding element, and a ratio of the inlet duct internal diameter to the inlet duct nominal diameter greater than one can be achieved by way of the provision of at least one groove-shaped flow guiding element.

In accordance with one refinement, the fan unit is further preferably a radial fan unit, that is to say the fluid is sucked in by the fan impeller in its axial direction and is ejected in its radial direction.

In some refinements of the invention, the fan impeller of the fan unit has a plurality of blade elements, the blade elements being equipped at least partially with in each case one winglet which runs at least in sections on at least one axial longitudinal side of the blade element.

Here, in some refinements of the invention, the winglet has an extent of from 1° to 20° of the circumference of the fan impeller.

In some refinements of the invention, the extent of the winglet increases from the radial inside of the fan impeller to the radial outside of the fan impeller.

In some refinements of the invention, the fan impeller is equipped with at least one disk on only one axial side, and the disk is arranged only on that axial side which lies opposite an axial side, equipped with the winglets, of the fan impeller.

BRIEF DESCRIPTION OF THE DRAWINGS

Further features and advantages of the invention result from the following description of exemplary embodiments of the invention which are not to be understood to be restrictive, which invention will be described in greater detail in the following text with reference to the drawing, in which, diagrammatically:

FIG. 2 shows a perspective partial view of the fan unit from FIG. 1, FIG. 3 shows a perspective partial view of a further embodiment of a fan unit according to the invention.

In the different figures, parts which are equivalent with regard to their function are always provided with the same designations, with the result that they are also as a rule described only once.

DETAILED DESCRIPTION OF EMBODIMENTS OF THE INVENTION

Figure 1:
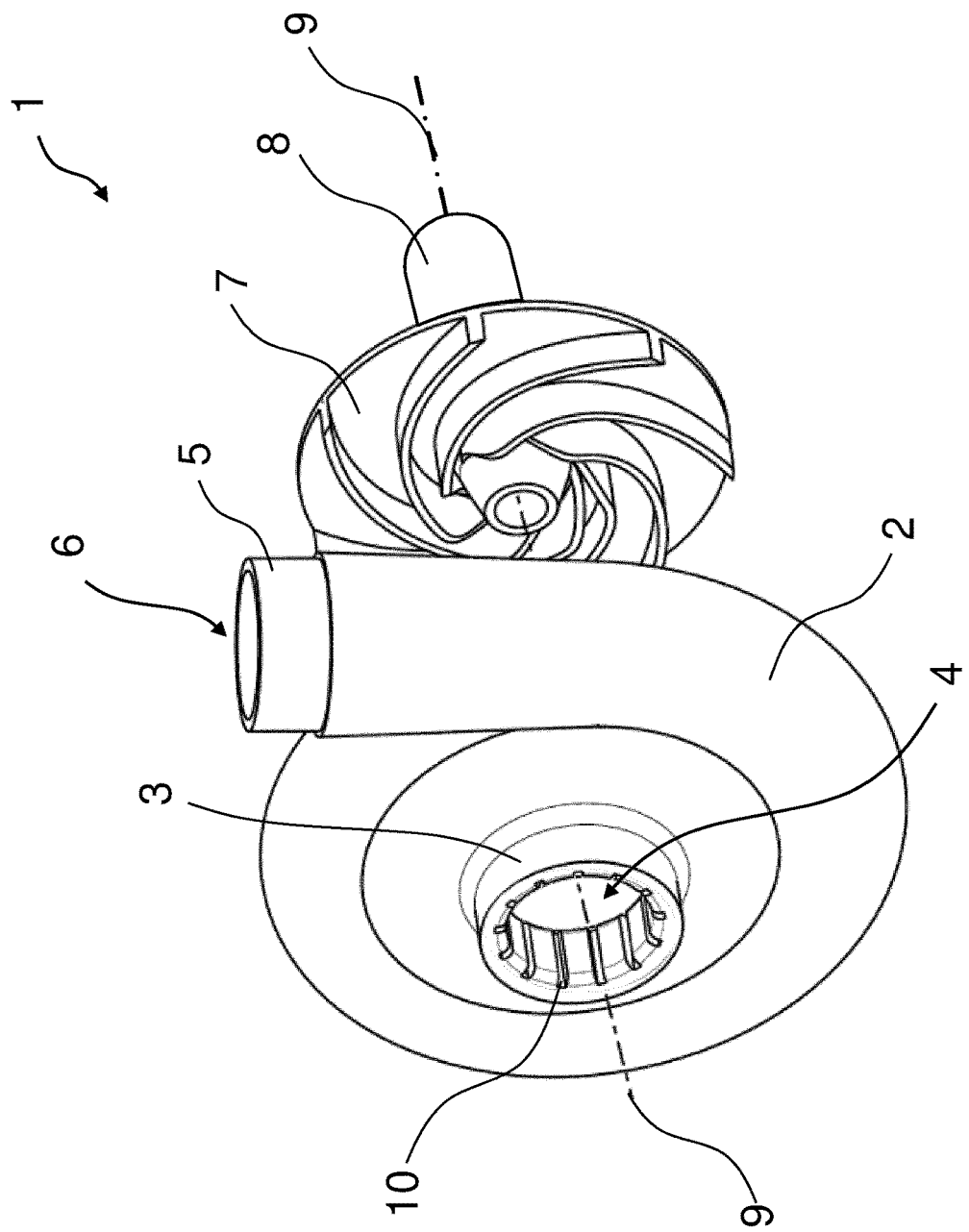
FIG. 1 shows an exploded view of one exemplary embodiment of the fan unit according to the invention.

FIG. 1 is an exploded view in a perspective illustration of one exemplary embodiment of the fan unit 1 according to the invention. The fan unit 1 can particularly preferably be used in a ventilator (not shown in further detail) for the ventilation of persons. As can be seen in FIG. 1, the illustrated fan unit 1 comprises a housing 2 with a suction connector 3 which forms an inlet duct 4 for the suction-side inflow of a fluid, in particular a breathing gas, into the housing 2. Furthermore, the fan unit 1 or the housing 2 comprises a pressure connector 5 which forms an outlet duct 6 for the pressure-side outflow of the fluid from the housing 2. Furthermore, it can be gathered from FIG. 1 that the fan unit 1 comprises a fan impeller 7 which is mounted rotatably in the housing 2 and, by way of rotation, sucks the fluid in via the suction connector 3 and conveys it through the inlet duct 4 into the housing 2 and subsequently ejects the fluid again via the pressure connector 5 and conveys it through the outlet duct 6 out of the housing. To this end, the fan impeller 7 is received substantially completely in the housing 2. In the case of the exemplary embodiment of the fan unit 1 shown in FIG. 1, the rotation is brought about via a drive motor 8, in particular an electric motor 8, which is not absolutely necessary, however. In addition, the electric motor 8 can likewise be received substantially completely in the housing 2 or can be arranged merely partially or else completely outside the housing 2 and can be connected in a driving manner to the fan impeller 7. As can be gathered from FIG. 1, moreover, the fan unit 1 is a radial fan unit, that is to say the fan impeller 7 is arranged in the housing 2 in such a way that the fluid is sucked in via the suction connector 3 in the axial direction of the fan impeller 7 and is ejected in the radial direction. In the case of the fan unit 1 which is shown in FIG. 1, the axial direction of the fan impeller 7 coincides with the center axis 9 of the fan unit 1 or the suction connector 3, without being restricted thereto, however.

Figure 5:
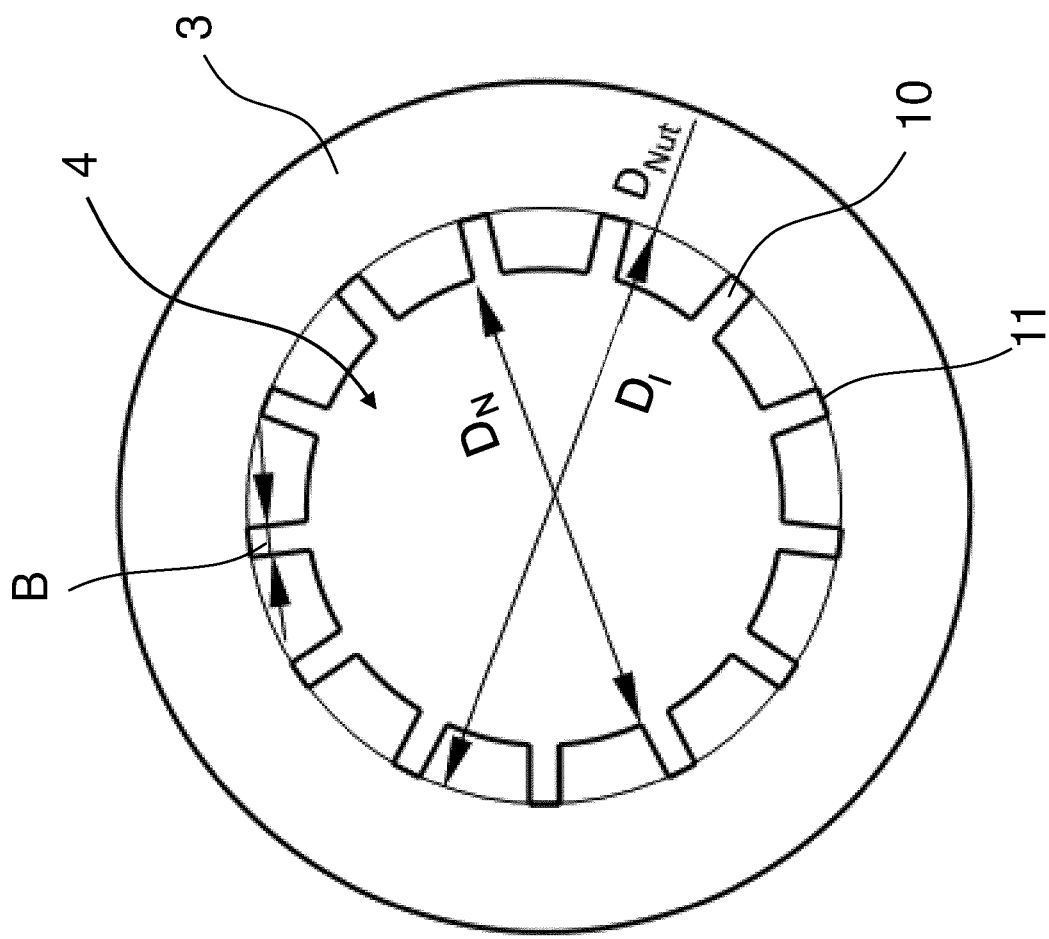
FIG. 5 shows a cross-sectional view through the suction connector of the fan unit from FIG. 2.

Furthermore, it can be gathered from FIG. 1 that the suction connector 3 has at least one flow guiding element 10, in the present case a plurality of flow guiding elements 10 on its inner face which faces the inlet duct 4 and sets or determines an inlet duct nominal diameter $D_N$ (see FIG. 5). In the case of the fan unit 1 which is shown in FIG. 1, the flow guiding elements 10 are configured as grooves. The flow guiding elements 10 or grooves 10 set an inlet duct internal diameter $D_I$ which differs from the inlet duct nominal diameter $D_N$, that is to say is greater in the present case than the inlet duct nominal diameter $D_N$. The plurality of grooves 10 are arranged distributed equidistantly over the circumference of the inner face of the suction connector 3, as can be seen clearly in FIG. 1.

FIG. 2 shows a perspective partial view of the fan unit 1 with the housing 2 from FIG. 1.

For comparison purposes with the fan unit 1 from FIG. 2, FIG. 3 shows a perspective partial view of a further exemplary embodiment of the fan unit 20 according to the invention. In contrast to the fan unit 1 from FIG. 2, in the case of a suction connector 21 of the fan unit 20, a plurality of flow guiding elements 22 are configured as ribs 22 which project from the inner face of the suction connector 21. In the case of the exemplary embodiment of the fan unit 20 shown in FIG. 3, a total of four ribs 22 of this type are shown, without being restricted to said number. The flow guiding elements 22 or ribs 22 set an inlet duct internal diameter $D_I$ which differs from the inlet duct nominal diameter $D_N$, that is to say which is smaller in the case of the present fan unit 20 than the inlet duct nominal diameter $D_N$. The (in the present case, four) ribs 22 are arranged distributed equidistantly over the circumference of the inner face of the suction connector 21, as can be seen clearly in FIG. 3. Since the ribs 22 of the fan unit 20 do not extend in the radial direction as far as the center axis 9 of the suction connector 21 and accordingly are not in contact with one another there, the inlet duct internal diameter $D_I$ which is set by way of the ribs 22 of the fan unit 20 is greater than zero.

Figure 4:
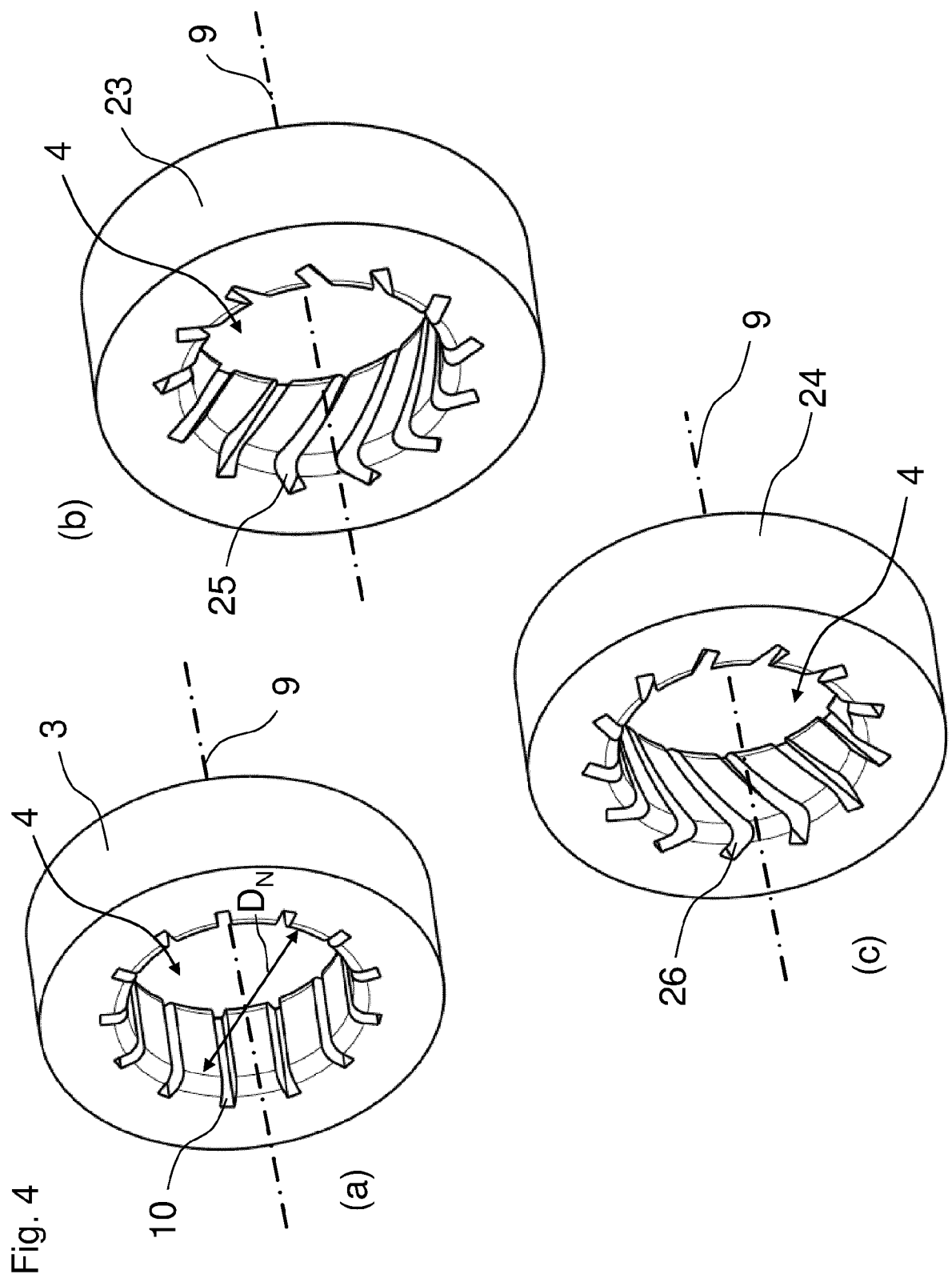
FIGS. 4(a)-(c) show a perspective detailed view of a suction connector of the fan unit from FIG. 2, a perspective detailed view of a suction connector of a further exemplary embodiment of a fan unit according to the invention, and a perspective detailed view of a suction connector of a further exemplary embodiment of a fan unit according to the invention.

FIG. 4 shows a perspective detailed view (a) of the suction connector 3 of the fan unit 1 from FIG. 2 and, furthermore, shows a perspective detailed view (b) of a suction connector 23 of a further exemplary embodiment of a fan unit according to the invention (not shown here in further detail) and a perspective detailed view (c) of a suction connector 24 of a further exemplary embodiment of a fan unit (likewise not shown in greater detail) according to the invention. The fan units which are not shown in the present case and in each case comprise the suction connectors 23 and 24 can be of identical construction to the fan unit 1 from FIG. 1 apart from the respective suction connectors 23 and 24.

In the case of the suction connector 3 of the fan unit 1, it can be seen clearly in FIG. 4(a) that the flow guiding elements 10 which are configured as grooves extend in their respective longitudinal extent directions parallel to the center axis 9 of the suction connector 3, that is to say accordingly run in an axially parallel manner. This refinement has proven to be particularly efficient with regard to as great a pressure increase as possible for the fluid which flows in the inlet duct 4. The flow guiding elements can have a straight course in their respective longitudinal extent directions.

Although the suction connector 23 from FIG. 4(b) likewise comprises flow guiding elements 25 which are configured as grooves, they do not run in their longitudinal extent directions in an axially parallel manner with respect to the center axis 9, but rather are inclined at an angle with respect to the center axis 9 of the suction connector 23. The angle of inclination of the grooves 25 with respect to the course of the center axis 9 is preferably more than 0° (0° corresponds to the axially parallel orientation) and less than or equal to 45°. The flow guiding elements can have a curved or bent course in their respective longitudinal extent directions. The flowing fluid can experience a boost or swirl as a result of the curved or bent course of the flow guiding elements.

In the case of the suction connector 24 in FIG. 4(c), the flow guiding elements 26 which are once again configured as grooves are likewise oriented inclined at an angle with respect to the center axis 9, but are inclined precisely in the opposite direction in comparison with the grooves 25 of the suction connector from FIG. 4(b). In this refinement, a preferred angle of inclination can accordingly be defined as an angle between less than 0° and greater than or equal to −45°.

FIG. 5 shows a cross-sectional view through the suction connector 3 of the fan unit 1 from FIG. 2. The inlet duct nominal diameter $D_N$ which is defined by way of the inner face of the suction connector 3 can be seen clearly in FIG. 5. The flow guiding elements 10 which are introduced into the inner face in the form of grooves set an inlet duct internal diameter $D_I$ which, in the case of the suction connector 10 of the fan unit 1 from FIG. 2, is greater than the inlet duct nominal diameter $D_N$ and is delimited by way of the groove bottom of the respective groove 10. Furthermore, in the cross-sectional view of FIG. 5, a width B of one of the flow guiding elements 10, that is to say its extent in the tangential direction of the suction connector 3 which is of hollow-cylindrical configuration in the present case or of its inner face, is specified. In the case of the exemplary embodiment which is shown, the width B of the flow guiding element 10 is a groove width B of the grooves 10. It is to be understood that the width of the flow guiding element 22 can also be understood as a web width or a rib width in the case of the fan unit 20 which is shown in FIG. 3. Accordingly, the flow element width is generally the extent direction of the respective flow guiding elements 10, 22, 25, 26 in the tangential direction of the respective suction connectors 3, 21, 23 and 24.

It has emerged, that in the case of a configuration of the flow guiding elements as grooves as in the case of the grooves 10 of the fan unit 1 which are oriented in an axially parallel manner, a maximum pressure gain or pressure rise in the inlet duct 4 can be achieved at a constant rotational speed of the fan impeller 7 in comparison with conventional suction connectors without flow guiding elements if a total of 13 axially parallel grooves 10 which are arranged distributed equidistantly along the inner circumference of the inner face of the suction connector 3 are provided in each case with a width B of from 0.3 to 2.1 mm, preferably from 0.5 to 1.5 mm, for example also from 0.8 to 1.2 mm. According to the invention, the width B is also always adapted in proportion to the number of grooves or ribs. According to the invention, the relation of the overall width B of the ribs (for example, eight 1 mm ribs) to the free diameter of the inflow duct is 8 mm to 16 mm, and the ratio of the inflow duct area to the area blocked by way of the ribs is preferably in the range from 1.1 to 1.6, for example also from 1.2 to 1.4 or approximately 1.2.

The diameter ratio of the inlet duct internal diameter $D_I$ to the inlet duct nominal diameter $D_N$ is from 1.05 to 1.6, preferably from 1.1 to 1.4, particularly preferably from 1.2 to 1.3.

In the case of flow guiding elements which are configured as ribs, such as, for example, in the case of the fan unit 20 which is shown in FIG. 3, a maximum pressure gain can be achieved in the inlet duct 4 by way of a total of eight ribs 22 which are arranged distributed equidistantly in the circumferential direction along the inner face of the suction connector 21.

In general, the ribs 22 might have any conceivable shape.

The end side 22a of the ribs is rounded, for example, on the side which faces the inflowing fluid.

The ribs can be angular and/or rounded at the inlet and outlet of the fluid.

The ribs can taper from the inlet toward the outlet of the fluid (or vice versa) and can therefore have a profile of the width B.

The ribs can have a symmetrical wing profile.

The ribs can be configured as a curved wing.

The ribs can be configured with notches over the axial running length.

The ribs can be configured with apertures/holes in the ribs, with the result that an exchange flow from one rib flow duct to the next is produced.

Figure 6:
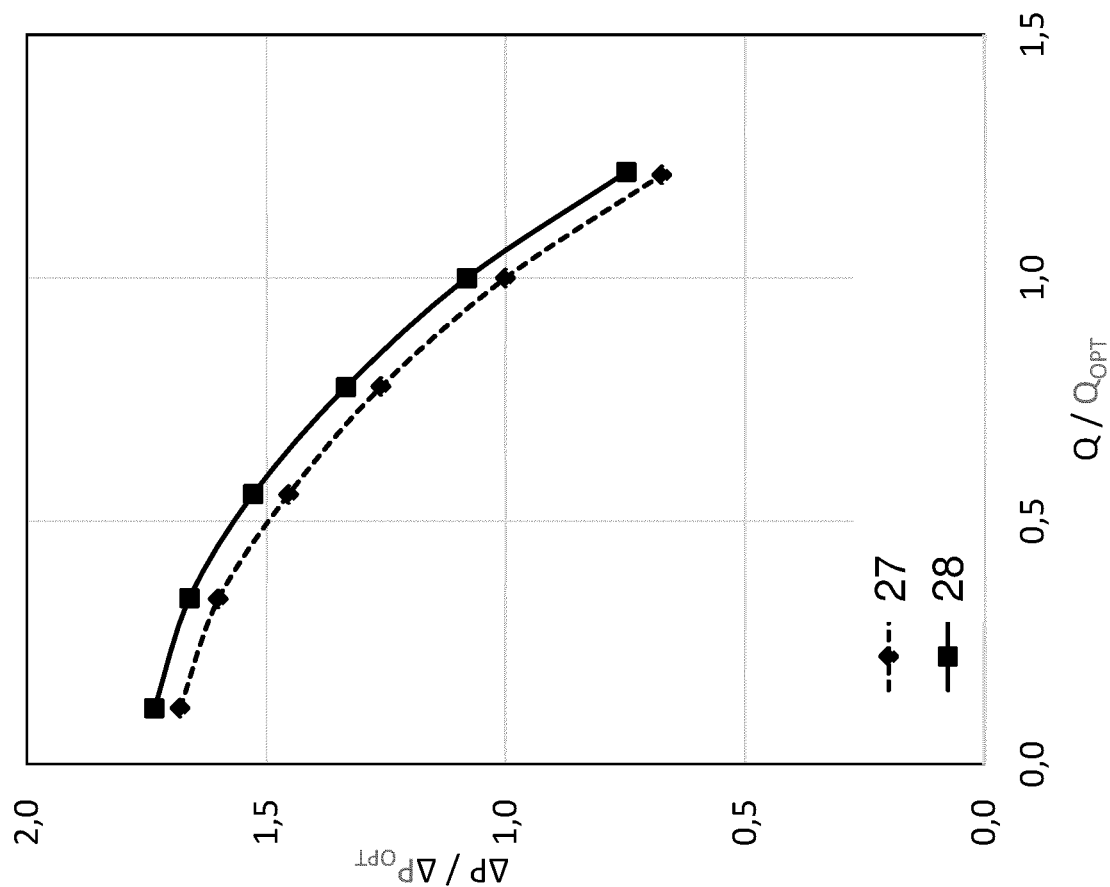
FIG. 6 shows a pressure diagram which illustrates a comparison of the fan unit from FIG. 2 with a fan unit in accordance with the prior art.

FIG. 6 illustrates a pressure diagram which shows a comparison of the fan unit 1 from FIG. 2 with a fan unit according to the prior art, the fan unit 1 comprising (as described above and as shown in FIG. 5) 13 axially parallel grooves 10 which are arranged distributed uniformly on the inner face of the suction connector 3 as flow guiding elements.

The pressure $\Delta p/\Delta p_{opt}$ which is standardized to an optimum operating point of the fan unit (not shown herein) according to the prior art, that is to say a fan unit with a suction connector without flow guiding elements in the sense of the invention, is plotted along the ordinate of the pressure diagram, and the volumetric flow $Q/Q_{opt}$ which is standardized to an optimum operating point of the fan unit according to the prior art is plotted along the abscissa. A pressure curve of the conventional fan unit according to the prior art is drawn as a dashed curve 27 in the pressure diagram, and a pressure curve of the fan unit 1 in accordance with an exemplary embodiment of the invention disclosed herein is drawn as a solid curve 28.

It can be seen clearly in FIG. 6 that, at $Q/Q_{opt}$=1.0, the optimum pressure $\Delta p/\Delta p_{opt}$ (likewise equal to 1.0) of the conventional fan unit (curve 27) is reached. In contrast, the curve 28 of the fan unit 1 in accordance with the exemplary embodiment of the invention described herein, reaches a considerably higher pressure at the same volumetric flow (=same rotational speed of the fan impeller 7), accordingly $\Delta p/\Delta p_{opt}$>1.0, in the present case approximately $\Delta p/\Delta p_{opt}$=1.1. In this way, a pressure increase of the fluid at the same rotational speed of the fan impeller 7 can be achieved solely by way of the provision of the flow guiding elements 10 in the inlet duct 4.

The fan unit according to the invention disclosed herein is not restricted to the embodiments disclosed herein, but rather also comprises identically acting further embodiments which result from technically appropriate further combinations of the features of the fan unit which are described herein. In particular, the features and combinations of features which are mentioned in the general description and the description of the figures and/or are shown alone in the figures can be used not only in the respective combinations specified explicitly herein, but rather also in other combinations or on their own, without departing from the scope of the present invention.

In one preferred embodiment, the fan unit according to the invention is used for operating ventilators for the ventilation of persons, for example persons with insufficient or suspended spontaneous respiration, by a fluid, in particular a breathing gas, being conveyed by means of the fan unit, that is to say being sucked in on the suction side and being discharged again on the pressure side at a predefined pressure, and subsequently being fed to the person using the ventilator.

Figure 7:
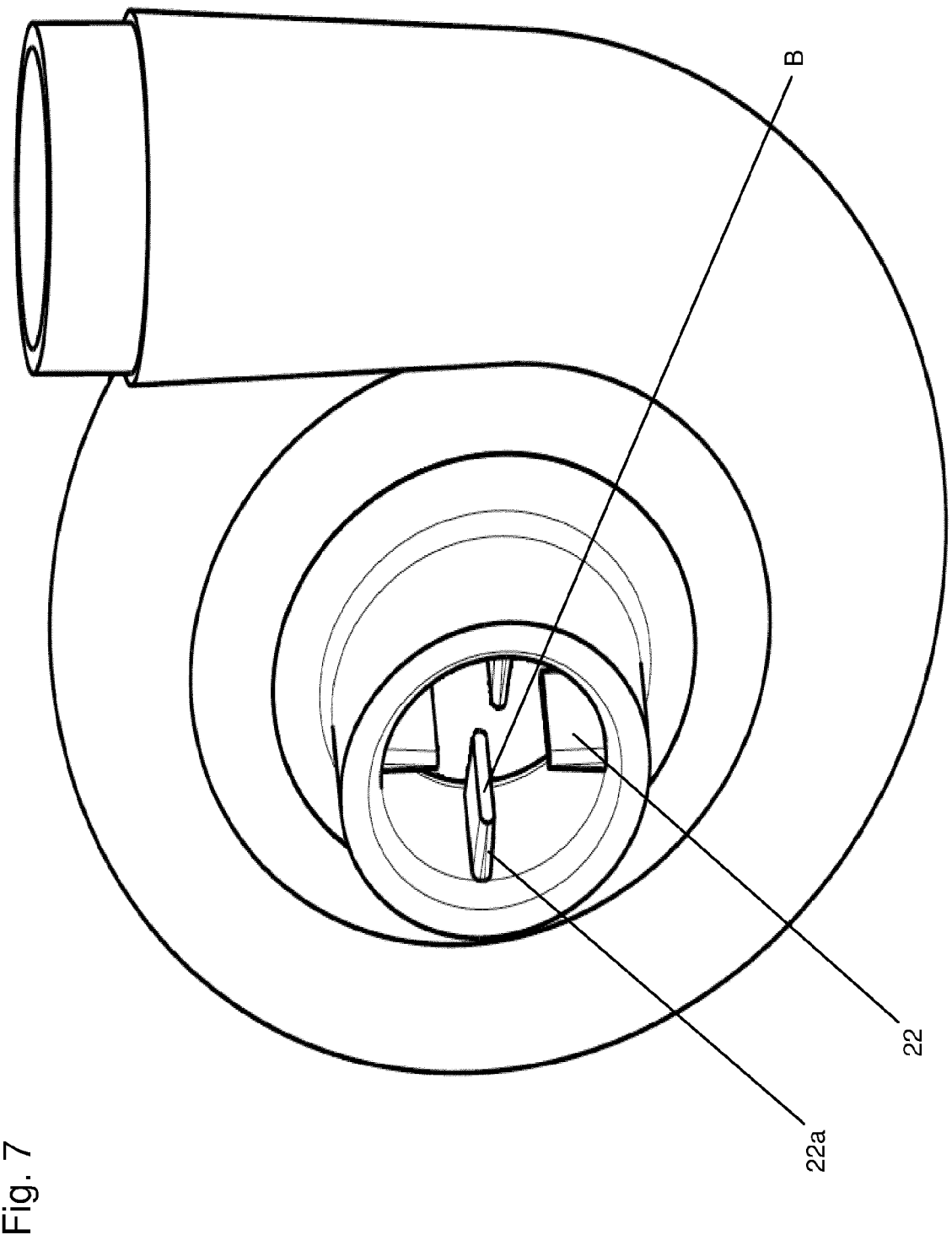
FIG. 7 shows a perspective view of one exemplary embodiment of a fan unit.

FIG. 7 shows, in the case of flow guiding elements which are configured as ribs, such as for example in accordance with the fan unit 20 which is shown in FIG. 3, that a maximum pressure gain can be achieved in the inlet duct 4 by way of a total of 2-30 ribs 22 which are arranged distributed equidistantly in the circumferential direction along the inner face of the suction connector 21.

In general, the ribs 22 might assume any conceivable shape.

The end side 22a of the ribs is rounded, for example, on the side which faces the inflowing fluid.

The ribs can be angular and/or rounded at the inlet and outlet of the fluid.

The ribs can taper from the inlet toward the outlet of the fluid (or vice versa) and can therefore have a profile of the width B.

The ribs can have a symmetrical wing profile.

The ribs can be configured as a curved wing.

The ribs can be configured with notches over the axial running length.

The ribs can be configured with apertures/holes in the ribs, with the result that an exchange flow from one rib flow duct to the next is produced.

The comments on FIG. 7 can likewise be applied to grooves.

In general, the flow guiding elements might assume any conceivable shape.

The end side 22a of the flow guiding elements is rounded, for example, on the side which faces the inflowing fluid.

The flow guiding elements can be angular and/or rounded at the inlet and outlet of the fluid.

The flow guiding elements can taper from the inlet toward the outlet of the fluid (or vice versa) and can therefore have a profile of the width B.

The flow guiding elements can have a symmetrical wing profile.

The flow guiding elements can be configured as a curved wing.

The flow guiding elements can be configured with notches over the axial running length.

The flow guiding elements can be configured with apertures/holes in the flow guiding elements, with the result that an exchange flow from one flow duct to the next is produced.

Figure 8:
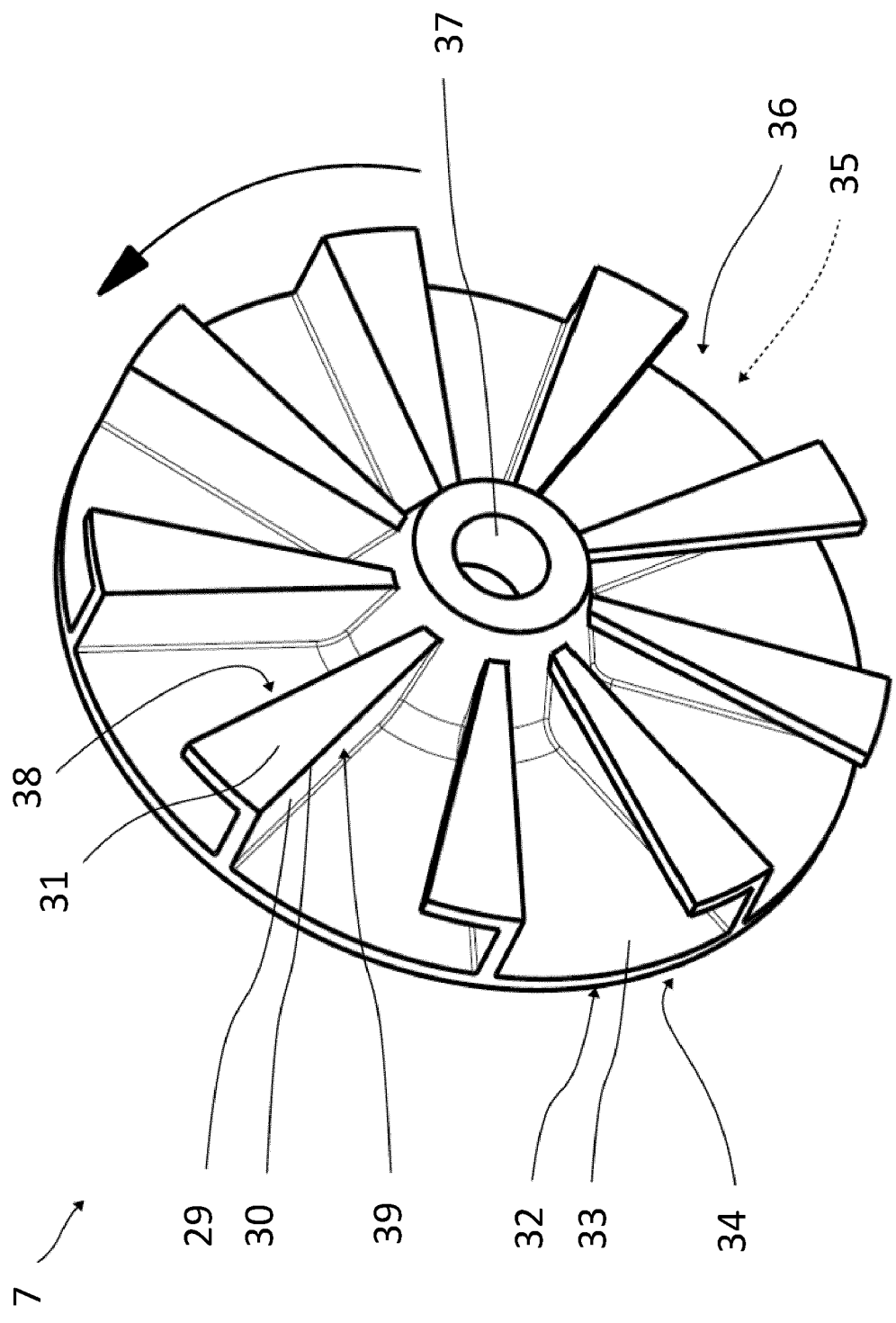
FIG. 8 shows a perspective view of a fan impeller.

FIG. 8 shows a fan impeller 7 in a perspective view. Here, the fan impeller 7 is equipped with a plurality of blade elements 29, a disk 32 which is configured as a carrying disk 33, and a hub 37 for connection to a drive shaft. Here, the blade elements 29 are fastened to the carrying disk 33 and preferably also to the hub 37, and, for example, are connected to them in one piece. The fan impeller 7 can also be configured without disks 32 and, in particular, without carrying disk 33, for example as a star fan impeller.

The preferred rotational direction of the fan impeller 7 is illustrated here by way of an arrow. The blade elements 29 have a suction side 38 and a pressure side 39. The orientation shown here of the suction side 38 and the pressure side 39 results for the rotational direction shown here of the fan impeller 7.

In order to effectively and reliably prevent the exchange flow from the side space and from the pressure side 39 to the suction side 38 in the direction of the side space or an axial side, the fan impeller 7 is equipped with winglets 31. Here, each blade element 29 is equipped with a winglet 31. The winglets 31 run in each case along an axial longitudinal side 30 of the blade element 29. In the refinement of the invention shown here, the winglets 31 point in the direction of the suction side 38 of the respective blade element 29. An advantageous pressure increase and also a considerable increase in the degree of efficiency could be observed for a fan impeller 7 of this type.

The fan impeller 7 shown here is integrated, for example, into the fan unit 1 in such a way that intake is carried out axially and ejection is carried out radially. Here, the intake side lies on the axial side 36 with the winglets 31.

In the refinement shown here, the fan impeller 7 is equipped with the disk 32 only on one axial side 34. Here, the disk 32 which is configured as a carrying disk 33 is arranged on that axial side 34 of the fan impeller 7 which lies opposite that axial side 36 of the fan impeller 7 which is equipped with the winglets 31.

In one development, a disk 32 which is not shown here in greater detail and is configured as a cover disk 35 can also be provided. Here, the cover disk 35 can be arranged in addition to the carrying disk 33 on the axial side 36 or can replace the carrying disk 33.

LIST OF REFERENCE NUMERALS

1 Fan unit
2 Housing
3 Suction connector
4 Inlet duct
5 Pressure connector
6 Outlet duct
7 Fan impeller
8 Drive motor 9 Center axis
10 Flow guiding element/groove
20 Fan unit
21 Suction connector
22 Flow guiding element/rib
23 Suction connector
24 Suction connector
25 Flow guiding element/groove
26 Flow guiding element/groove
27 Pressure curve of a fan unit according to the prior art
28 Pressure curve of 1
29 Blade element
30 Longitudinal side
31 Winglet
32 Disk
33 Carrying disk
34 Side
35 Cover disk
36 Side
37 Hub
38 Suction side
39 Pressure side
B Width of a flow guiding element
$D_I$ Inlet duct internal diameter
$D_N$ Inlet duct nominal diameter
Δp Pressure
$Δp_{opt}$ Pressure at an optimum operating point of a fan unit according to the prior art
Q Volumetric flow
$Q_{opt}$ Volumetric flow at an optimum operating point of a fan unit according to the prior art

What is claimed is:

1. A fan unit for a ventilator, wherein the fan unit comprises a housing with a suction connector which forms an inlet duct for a suction-side inflow of a fluid into the housing, and a pressure connector which forms an outlet duct for a pressure-side outflow of the fluid from the housing, as well as a fan impeller which is mounted rotatably in the housing and is configured and arranged, by way of rotation, to suck in the fluid via the suction connector and to convey it through the inlet duct into the housing, and to eject the fluid again via the pressure connector and to convey it through the outlet duct out of the housing, the suction connector comprising at least one flow guiding element on its inner face which faces the inlet duct and defines an inlet duct nominal diameter ($D_N$), the at least one flow guiding element setting an inlet duct internal diameter ($D_I$) which differs at least in sections from the inlet duct nominal diameter ($D_N$).

2. The fan unit of claim 1, wherein a diameter ratio of the inlet duct internal diameter $D_I$ to the inlet duct nominal diameter $D_N$ is from 1.05 to 1.6.

3. The fan unit of claim 1, wherein the at least one flow guiding element is a groove which is made in the inner face and increases the inlet duct internal diameter ($D_I$) in comparison with the inlet duct nominal diameter ($D_N$).

4. The fan unit of claim 1, wherein the at least one flow guiding element is a rib which projects from the inner face and reduces the inlet duct internal diameter ($D_I$) in comparison with the inlet duct nominal diameter ($D_N$).

5. The fan unit of claim 1, wherein a plurality of flow guiding elements including the at least one flow guiding element are arranged distributed equidistantly over a circumference of the inner face.

6. The fan unit of claim 1, wherein the at least one flow guiding element has an end side, said end side being rounded on a side which faces the inflowing fluid.

7. The fan unit of claim 1, wherein the at least one flow guiding element comprises two end sides, one end side that is on a side which faces the inflowing fluid being rounded or angular, and the other end side that is on a side which faces away from the inflowing fluid being rounded or angular.

8. The fan unit of claim 1, wherein the at least one flow guiding element has a symmetrical wing profile and/or is configured as a curved wing and/or is configured with notches over an axial length.

9. The fan unit of claim 1, wherein the at least one flow guiding element is configured with apertures/holes therein, with the result that an exchange flow from one flow duct to the next is produced and/or wherein the at least one flow guiding element tapers in the flow direction of the fluid (or vice versa).

10. The fan unit of claim 1, wherein the at least one flow guiding element has a width B, that is to say its extent in the tangential direction of the suction connector or its inner face.

11. The fan unit of claim 1, wherein the at least one flow guiding element has a width B with a course of the width B and/or has a width B ranging from 0.4 mm to 2.2 mm.

12. The fan unit of claim 11, wherein ribs extend in a radial direction as far as a center axis of the suction connector and are in contact with one another there.

13. The fan unit of claim 1, wherein the at least one flow guiding element extends in its longitudinal extent direction parallel to a center axis of the suction connector.

14. The fan unit of claim 1, wherein the at least one flow guiding element extends in its longitudinal extent direction at an angle in an inclined manner with respect to a center axis of the suction connector.

15. The fan unit of claim 14, wherein the angle is greater than 0° and less than or equal to 45°.

16. The fan unit of claim 1, wherein the ratio between the inlet duct internal diameter ($D_I$) and the inlet duct nominal diameter ($D_N$) is from 0.6 to 1.4.

17. The fan unit of claim 1, wherein the fan unit is a radial fan unit.

18. The fan unit of claim 1, wherein a fan impeller comprises a plurality of blade elements, the blade elements being equipped at least partially with in each case one winglet which runs at least in sections on at least one axial longitudinal side of the blade element.

19. The fan unit of claim 18, wherein the winglet has an extent of from 1° to 20° of a circumference of the fan impeller and/or wherein the extent of the winglet increases from a radial inside of the fan impeller to a radial outside of the fan impeller.

20. The fan unit of claim 1, wherein a fan impeller is equipped with at least one disk on only one axial side, and the disk is arranged only on that axial side which lies opposite an axial side, equipped with the winglets, of the fan impeller.

* * * * *